Dec. 31, 1963 G. A. MOODY Plant Pat. 2,336

PEACH TREE

Filed Oct. 15, 1962

WITNESS

Addison I. Avery

INVENTOR

Glen A. Moody

Webster & Webster

ATTYS.

United States Patent Office

Plant Pat. 2,336
Patented Dec. 31, 1963

2,336
PEACH TREE

Glen A. Moody, Rte. 2, Box 551, Bakersfield, Calif.

Filed Oct. 15, 1962, Ser. No. 230,774
1 Claim. (Cl. Plt.—43)

This discovery relates to a new and distinct variety of hardy, vigorous, productive peach tree which bears medium size yellow flesh fruit having yellow skin overspread to a substantial extent with a red blush; the stone being semi-free when the fruit is hard ripe and free when full ripe.

Additionally, the fruit of the present variety of peach tree is of good market quality, ripens evenly, keeps and ships well, and does not oxidize or turn brown when cut and held under refrigeration; the yellow flesh being firm but melting, and of fine uniform texture.

The present variety originated as a bud mutation of the Coronet (unpatented), and in general the tree and fruit of the present variety bear close resemblance thereto; the primary distinctive characteristic being in the comparative ripening periods of the yellow flesh fruit. More particularly, the fruit of the present variety of peach tree ripens approximately eight days earlier than the Coronet, and which is of commercial advantage.

Other distinguishing characteristics, in comparison to the Coronet, are reflected in the fruit which has a smaller stone, slightly more of a point at the apex, and while mild, a somewhat stronger flavor.

The present variety of peach tree was discovered by me as a bud mutation on a mature Coronet tree in an orchard on my farm located near Bakersfield, California. After discovery of such bud mutation, and recognition by me of its distinctive characteristics, I asexually reproduced the variety by grafting onto several mature orchard trees on my farm located as aforesaid, and in maturity such reproductions were found to run true in all respects. Subsequent asexual reproductions, by budding, conducted on my behalf by a commercial nursery, have also run true.

Figure 1:
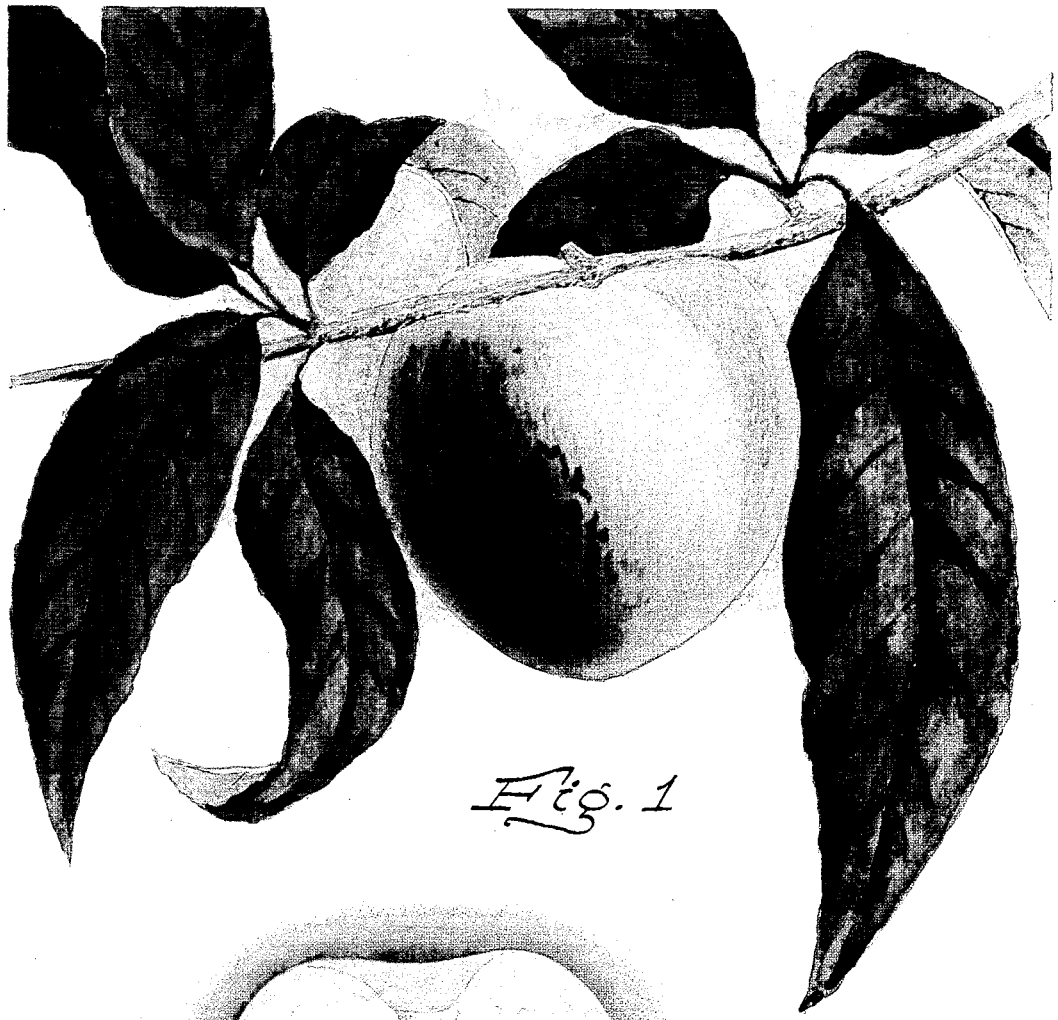
FIG. 1 is an elevation showing one of the peaches together with a twig and leaves.
Figure 2:
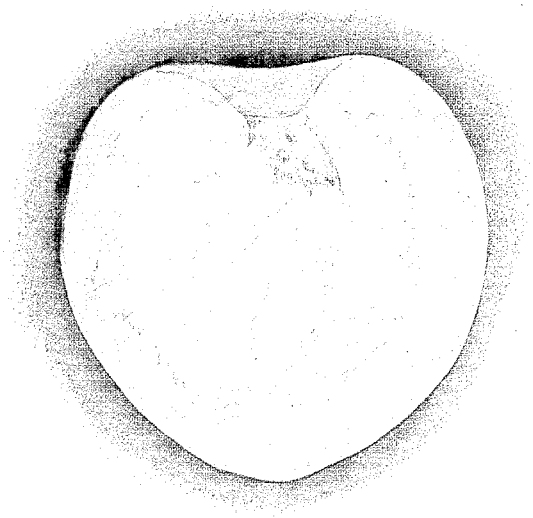
FIG. 2 is a sectional elevation of one of the peaches with the stone remaining in place and partially showing.

Referring now more specifically to the pomological details of this new and distinct variety of peach tree, the following is an outline description thereof; all major color plate identifications being by reference to Maerz and Paul Dictionary of Color, except where common terms of color definition are employed.

Tree:
- *Size.*—Large.
- *Vigor.*—Vigorous.
- *Growth.*—Upright.
- *Density.*—Dense.
- *Shape.*—Vase formed.
- *Hardiness.*—Not determined.
- *Production.*—Productive.
- *Bearing.*—Regular bearer.

Trunk:
- *Size.*—Medium.
- *Surface.*—Medium.

Branches:
- *Size.*—Medium.
- *Surface.*—Medium.
- *Color.*—Gray.
- *Lenticels.*—Number—numerous. Size—small.

Leaves:
- *Size.*—Large. Average length—6". Average width—1½".
- *Form.*—Lanceolate, acutely pointed.
- *Thickness.*—Thin.
- *Surface.*—Smooth.
- *Margin.*—Finely serrate.
- *Petiole.*—Medium length; medium thickness.
- *Glands.*—Average number—three. Alternate; small; reniform; brown; positioned at juncture of leaf with petiole and on both thereof.
- *Stipules.*—None.
- *Color.*—Top side—medium green (22–L–6). Under side—lighter green (21–J–5).

Flower buds:
- *Hardiness.*—Not determined.
- *Size.*—Medium.
- *Length.*—Medium.
- *Form.*—Plump; free.

Flowers:
- *Blooming period.*—Date of first bloom—March 6, 1962. Date of full bloom—March 15, 1962. Early as compared with other varieties.
- *Size.*—Medium.
- *Color.*—Pink.

Fruit:
- *Maturity when described.*—Eating-ripe.
- *Date of first picking for market.*—June 2, 1962.
- *Date of last picking for market.*—June 8, 1962.
- *Comparative harvest.*—Approximately eight days earlier than the Coronet.
- *Size.*—Uniform; medium. Average diameter axially—2¾". Average transversely in suture plane—2¾".
- *Form.*—Uniform; symmetrical. Ovate—nearly round.
- *Suture.*—Extends from base to apex; shallow; no depression beyond pistil point.
- *Ventral surface.*—Rounded slightly; left lip slightly larger.
- *Cavity.*—Rounded. Elongated in suture plane, with suture showing on one side. Average depth—¼". Average breadth—¾". No markings.
- *Base.*—Rounded.
- *Apex.*—Mammiform.
- *Pistil point.*—Apical.

Skin:
- *Thickness.*—Medium.
- *Texture.*—Medium.
- *Tenacity.*—Free.
- *Tendency to crack.*—None.
- *Down.*—Scant; short; does not roll up when rubbed.
- *Color.*—Yellow ground color (10–L–6 to 11–L–10) overspread on approximately three-fourths of the surface with a bright red (5–L–8), with some red stripes (2–K–9), and darker red mottling (8–L–6) when fully ripe; such mottling being a substantially lighter red when hard ripe. A distinct light colored line extends along suture.

Flesh:
- *Amygdalin.*—Wanting.
- *Juice.*—Moderate.
- *Texture.*—Firm; fine; melting.
- *Fibers.*—Few; fine; tender.
- *Ripens.*—Evenly.
- *Flavor.*—Mild.
- *Aroma.*—Distinct.
- *Eating quality.*—Good.
- *Color.*—Yellow (10–K–5) with small areas of pale pink (2–C–1). When full ripe and cut, shades near skin to a light red (2–H–10). Surface of pit cavity, yellow.

Stone:
- *Type.*—Semi-free when hard ripe; free when full ripe; retains short fiber-like threads along ridges.
- *Size.*—Medium. Average length—1½". Average breadth—1". Average thickness—⅝".

*Form.*—Elliptical.

*Base.*—Straight.

*Hilum.*—Oblong.

*Apex.*—Acuminate.

*Sides.*—Equal.

*Surface.*—Irregularly furrowed near base; pitted throughout.

*Ridges.*—Rounded; interrupted.

*Pits.*—Elongated.

*Ventral edge.*—Thick.

*Dorsal edge.*—Narrow, with deep groove.

*Tendency to split.*—Slight.

*Color.*—Light tan (3–A–9).

Use: Market.

Keeping quality: Good.

Shipping quality: Good.

The tree and its fruit herein described may vary in slight detail due to climatic and soil conditions under which the variety may be grown; the present description being of the variety as grown near Bakersfield, California.

The following is claimed:

A new and distinct variety of peach tree, as illustrated and described, which is vigorous, and productive of medium size yellow flesh fruit having a yellow skin overspread to a substantial extent with a red blush, the stone being semi-free when the fruit is hard-ripe, and free when full-ripe; the variety being characterized—in comparison to the Coronet—by general resemblance in tree and fruit but primarily distinctive in the comparative ripening periods, the fruit ripening approximately eight days earlier than said Coronet.

No references cited.